United States Patent [19]

Vasington et al.

[11] Patent Number: 5,387,522
[45] Date of Patent: Feb. 7, 1995

[54] APPARATUS HAVING A BIPHASIC SPRAY HEAD FOR ENTRAPPING BIOLOGICAL MATERIAL IN A HYDROPHILIC GEL

[75] Inventors: Paul J. Vasington, Norwood, Mass.; Maurice M. Lynch, Warwock, R.I.; Maureen E. Frye, Mansfield, Mass.

[73] Assignee: Schering Corporation, Kenilworth, N.J.

[21] Appl. No.: 734,070

[22] Filed: Jul. 22, 1991

Related U.S. Application Data

[63] Continuation of Ser. No. 453,048, Dec. 13, 1989, abandoned, which is a continuation of Ser. No. 829,121, Jan. 14, 1986, abandoned, which is a continuation-in-part of Ser. No. 616,534, Jun. 1, 1984, Pat. No. 4,778,749.

[51] Int. Cl.$^6$ .................. C12M 1/00; C12M 1/40; C12N 11/10; C12N 5/00
[52] U.S. Cl. .................. 435/287; 435/174; 435/178; 435/182; 435/240.1; 435/240.22; 435/252.1; 435/254.1; 435/288
[58] Field of Search .............. 435/178, 182, 240.22, 435/288, 948, 287, 240.1, 252.1, 254.1

[56] References Cited

U.S. PATENT DOCUMENTS

| | | | |
|---|---|---|---|
| 4,352,883 | 10/1982 | Lim | 435/182 |
| 4,373,027 | 2/1983 | Berneman | 435/240 |
| 4,399,219 | 8/1983 | Weaver | 435/34 |
| 4,401,755 | 8/1983 | Weaver | 435/34 |
| 4,407,957 | 10/1983 | Lim | 435/178 |
| 4,409,331 | 10/1983 | Lim | 435/178 |
| 4,452,892 | 6/1984 | Rosevear | 435/176 |
| 4,495,288 | 1/1985 | Jarvis et al. | 435/174 |
| 4,603,054 | 7/1986 | Schmidt et al. | 476/574 |
| 4,778,749 | 10/1988 | Vasington et al. | 435/2 |

FOREIGN PATENT DOCUMENTS

| | | | |
|---|---|---|---|
| 8200660 | 3/1982 | WIPO | 435/240.22 |

OTHER PUBLICATIONS

Immobilized Plant Cells For The Production and Transformation of Natural Products, FEBS Lett., vol. 103, Jul. 1979.
Methods for ImmobilizIng animal cells, TIBTECH, vol. 5, Mar. 1987.
Entrapment of animal cells for production of monoclonal antibodies and other biomolecules, Nature, vol. 302, Apr., 1983.

*Primary Examiner*—David M. Naff
*Attorney, Agent, or Firm*—Matthew Boxer; John J. Maitner; Eric S. Dicker

[57] ABSTRACT

Biological material is entrapped in a hydrophilic gel by using an apparatus containing a biphasic spray head. In a preferred embodiment, mammalian cells are mixed with a solution of alginate to form a mixture and the mixture is fed to a biphasic spray head where the mixture passes through a nozzle surrounded by an annular passageway through which air is passed. Droplets of the mixture are formed at the tip of the nozzle and air passing through the passageway frees the droplets from the tip and propels them into the atmosphere in the form of fine spherical droplets. The droplets then contact a solution of divalent cation such as calcium chloride which gels the alginate. Preferably, the nozzle has an inner diameter of between about 0.006" and 0.016" and is beveled at an angle between about 15° and 30° to form a conical tip.

6 Claims, 3 Drawing Sheets

APPARATUS HAVING A BIPHASIC SPRAY HEAD FOR ENTRAPPING BIOLOGICAL MATERIAL IN A HYDROPHILIC GEL

This application is a continuation of application Ser. No. 07/453,048, filed Dec. 13, 1989, which is a continuation of application Ser. No. 06/829,121, filed Jan. 14, 1986, both now abandoned. Ser. No. 829,121 is in turn a continuation of PCT/US85/00838, filed May 8, 1985; which in turn is a continuation-in-part of U.S. application Ser. No. 06/616,534, filed Jun. 1, 1984, now U.S. Pat. No. 4,778,749.

FIELD OF THE INVENTION

The present invention relates to a process for entrapment and growing cells and tissues in an artificial environment. More particularly, the present invention deals with methods and related products for entrapping living biological materials such as tissues and cells in a permeable gel-like material, nurturing and growing such cells within the gel-like mini-environment while supplying needed nutrients and other materials through the permeable gel from a macro-environment, and harvesting the metabolic and/or other products or by-products. The present invention permits in vitro cell culture and growth to high cell densities, increased yields of biologically produced products and many other benefits.

BACKGROUND OF THE INVENTION

Over the years, there has been considerable interest in the encapsulation or immobilization of living cells, particularly those of microbial origin. See generally, K. Mosbach, Ed., *Methods in Enzymology*, Vol. 44, Academic Press, New York, 1976; B. J. Abbott, *Ann. Rpt. Ferm. Proc.*, 2: 91 (1980); R. A. Messing, *Ann. Rpt. Ferm. Proc.*, 4: 105 (1980); Shovers, et al. U.S. Pat. No. 3,733,205 (1973). Interest has been extended to the immobilization of plant cells in suspension. P. Brodelius et al., *FEBS Letters*, 103, 93–97 (1979).

More recently, efforts have been concentrated in processes for encapsulating tissue and individual cells, particularly mammalian cells, so that they remain viable and in a protected state within a membrane which is permeable to the plethora of nutrients and other materials required for normal metabolic functions.

One such technique is described in U.S. Pat. No. 4,391,909 (Lim), wherein tissue cells such as Islet of Langerhans cells are encapsulated within a spherical semipermeable membrane comprising a polysaccharide having acidic groups which have been cross-linked for permanance of the protective membrane. The semipermeable membrane has a selected limit of permeability of no greater than about 200,000 daltons, so that serum proteins and other high molecular weight materials necessary for growth can be sealed with the living cells within the semipermeable membrane, while other, smaller molecular weight metabolites and nutrients can traverse the membrane wall and be interchanged with the outside media. The process therein disclosed comprises suspending the tissue to be encapsulated (and the high molecular weight nutrients) in a physiologically compatible medium containing a water soluble substance that can be made insoluble in water (i.e., gelled), to provide a temporary protective environment for the tissue. The medium containing the tissue is next formed into droplets by forcing the tissue-medium-nutrient suspension through a teflon coated hypodermic syringe, the tip of which is subjected to laminar air flow which acts as an air knife. See also U.S. Pat. No. 4,352,883, wherein the spheres are formed by forcing the materials through a capillary tube into the center of a vortex created by rapidly stirring a solution of $Ca++$ cation. The medium, e.g. a polysaccharide gel, is temporarily gelled in a generally spherical shape by contact with the calcium solution. Thereafter, these "temporary capsules" are provided with permanant polymeric semipermeable membranes at their outer layer, formed by permanently cross-linking or polymerizing the capsules with polymers containing reactive groups which can react with specific constituents of the polysaccharide.

Thus until the present invention, entrapment in alginate gels alone was considered as only a "temporary" vehicle, around which a permanent membrane could be formed. Generally, following the formation of the permanent membrane, the "temporary" gel was dissolved, so that any cell growth achieved thereafter was not in the presence of the gelled substance.

Such complex prior art processes are not without limitations. For instance, with mammalian cells, although it has been possible to encapsulate viable cells within hardened semipermeable membranes, promotion of growth therein has not been satisfactory. Moreover, cell densities thus far achievable within such membranes has been less than about $10^6$ viable cells per milliliter of culture media. Both of these limitations affect the amount and recovery of useful and desirable cell products produced by the entrapped material. The ability to grow cells to higher cell densities within a protected environment (capsule) would provide a means for achieving greater output of desirable cell products.

A further disadvantage of prior art methods of entrapping animal cells is the inability to maintain cell viability at desirable higher cell densities. See P. Brodelius et al., *FEBS Letters*, supra, where entrapment of mammalian cells resulted in a lack of proliferation of cells and a cell viability of about 10–30% after incubation in tissue culture for one (1) week.

SUMMARY OF THE INVENTION

In one aspect, the present invention provides a process for proliferating cells within an artificial gel-like environment. The methods and products involved permit the growth of mammalian cells in in vitro tissue culture media to greater than normal (unentrapped) cell densities, the maintenance of high cell viability in such material, and the collection of by-products produced as a result of entrapped cell metabolism.

The basic approach involves suspending the cells in a polysaccharide gum, preferably an alkali metal alginate such as sodium alginate and thereafter forming the suspension into droplets. The droplets thus formed are gelled in a calcium chloride solution, washed and grown in culture media to proliferate cells entrapped therein.

More specifically, the present invention provides a process for proliferating viable mammalian cells (including hybridoma cells) within a semipermeable gel-like membrane. As noted above, it has previously been difficult to maintain viable mammalian cells in an artificial environment at levels greater than 10–30% viability. It has also been extremely difficult to grow mammalian cells in artificial environments, i.e. capsules, particularly at cell densities where commercial quantities of cell products are produced. The present invention overcomes such obstacles in that it allows entrapment of viable mammalian cells at viabilities exceeding 50% and at cell densities where desirable cell products can be economically harvested for commercial use.

In another aspect of the present invention, there is provided a process for producing substances which are produced by viable cells which comprises the above-described entrapment technique.

DETAILED DESCRIPTION OF THE INVENTION

Figure 1:
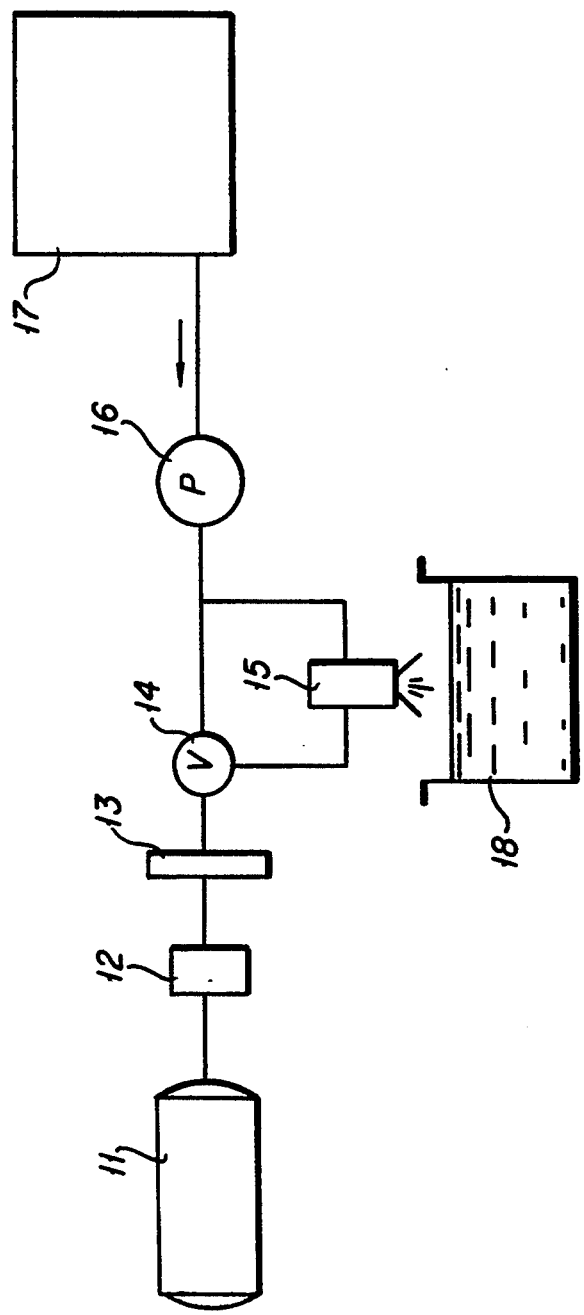
FIG. 1 shows a schematic depiction of one embodiment of various apparatus which are useful in connection with the present invention.

It has now been discovered that mammalian and other living cells can be entrapped in hydrophilic gels by a method and using apparatus which is much simpler than those previously used; that such entrappeal cells can be grown to large cell densities and maintained for substantial periods of time, without the need for an additional selectively permeable membrane surrounding the entrapped cells; that such entrapped cells can be used to produce high levels of metabolic or other cellular products, such as monoclonal antibodies; and that, after a suitable period wherein the production of the desired material(s) is maximized, the used but viable cells can be recovered for re-use by resolubilizing the hydrophilic gel to release the entrapped cells, followed by re-entrapment using the same procedure, as described above.

The present invention is particularly well suited for the production of monoclonal antibodies using hybridomas entrapped in a hydrophilic gel. However, other cell types, particularly mammalian can also be used to advantage to produce other products in accordance with the present invention. Other types of cells which can be used to produce desired products include various types of T-cells, e.g. helper T-cells, suppressor T-cells, B-cells, mast and stem cells, hormone-producing cells from the pituitary or other glands or tissues in the body; and other tissue which produces or can be modified to produce the product of interest.

The hydrophilic gel used for entrapment is preferably an alginate, which is a natural hydrocolloid derived from seaweed, although other hydrophilic materials such as agarose, agar, carrageenan, chitosan, xanthan gum, polyacrylamides, poly HEMA, and others known in the art can be used to advantage in particular environments.

Preferably, the micro-environments which contain the cells, the hydrophilic gelling agent and various nutrients and accessory materials, are formed into discrete particles, preferably generally spherically-shaped particles. Preferably, the gelled particles are mobile and thus can be arranged for convenient culturing, treatment and product extraction. Thus, for example, the entrapment beads can be arranged, nurtured, or extracted in packed beds, fluidized beds, in stirred containers, in continuous reactors or treatment units, which themselves are known in the art, e.g. similar to those used for treating ion exchange resins, etc. The conditions of treatment, including temperature, pressure, solvent, and physical treatment should be chosen so that the entrapment beads retain their particulate nature.

The condition of treatment of the entrapped beads should also be chosen to maintain viability and growth of the cells contained within the beads. Thus, the beads should not be exposed to extremes of temperature pH, or to toxic chemicals, for amounts of time which would cause loss of viability of the desired cells. Temperature may range broadly from about 5° C. to about 45° C., preferably between about 15° C. and about 40° C. For many cell systems, growth is optimized at temperatures around 37° C. The pH at which the entrapment gels are maintained may also range broadly between about 5 and 9, preferably between about 6 and 8. Various steps in treatment of the beads may require different pH's, and pH values outside of the broad ranges can often be tolerated by the cells for limited periods of time without deleterious effect.

Cell viability and growth normally require access to a source of oxygen for respiration, as well as various nutrients, vitamins, amino acids, salts, and other components, known per se for various cell types. Normally some of these nutrients and other factors will be entrapped within the bed along with the cells, so that continuous growth for some periods of time can be maintained without further additions of such factors. However, culture of such cells for production of proteins or other metabolites or products require considerable time, and such production is normally optimized by providing the cells with ready access to the required nutrients and other ingredients. Thus, the entrapped beads are preferably suspended in or otherwise contacted with a fluid containing oxygen, nutrients, vitamins, minerals, etc., which can diffuse through the hydrophilic gel to the cells and thus maintain viability and growth.

As shown in FIG. 1, one apparatus utilized in entrapping cells in accordance with the present invention involves a controlled source of sterile air, means for admixing the cells to be grown with the hydrophilic gel-forming material while such material is in liquid form, means for feeding the sterile air and admixed cells/hydrocolloid to a standard gas/liquid atomizing spray head, and a reservoir of material which receives and gels the droplets formed by the spray head.

Thus, as shown schematically in FIG. 1, the apparatus used in the preferred embodiment comprises a compressor or other source of compressed air 11, an air flow meter 12, an air filter 13, which has an effective pore size of 0.22 um (micron) or less, so as to sterilize the air used. The sterilized air then proceeds through a control valve 14, to a conventional two-phase spray head 15, where it mixes with the liquid cell/hydrocolloid mixture.

The liquid cell/hydrocolloid mixture is preferably formed in a tank 17, and is fed to spray head 15 through a pump 16, which is preferably a controlled constant volume, peristaltic pump as is known in the art.

In the spray head 15, the liquid is forced out a small diameter (0.006–0.016 mil) cylindrical top, which is surrounded by an annular air passageway. The air contacting the droplets formed at the end of the top frees the droplets from the tips. The droplets are then propelled out into the atmosphere in the form of fine spherical droplets. The droplets then contact the liquid in container 18, which contains a divalent cation gelling agent, which gels the liquid droplets, such as a calcium chloride solution, where the hydrocolloid used is sodium alginate. Other divalent cation gelling agents include the other alkaline earth metals (except magnesium), other divalent metals, and divalent organic cations, such as ethylene disamine. Preferably, tank 17 and container 18 are both stirred during the process at slow speed, in order to keep the solids from settling out and to maintain constant concentration.

As noted above, previous attempts to grow mammalian cells in hydrogels, particularly without a porous outer semipermeable membrane, have met with little or no growth rate and poor viability. It has now been found that, by controlling particle size and the type of hydrogel used, mammalian cells can be entrapped or encapsulated and grown to high densities, with substantially improved viability of cells.

One important factor is the type of hydrocolloid to be used. Highly preferred are clarified long-chain sodium alginates, such as Kelco-Gel HV and Kelco-Gel LV, sold by Kelco Company (San Diego). These are sodium alginates which are fibrous in nature, are supplied at a neutral pH, (typically about 7.2) and contain approximately 80% carbohydrates, 9.4% sodium, 0.2% calcium, 0.01% magnesium, and 0.1% potassium. Kelco-Gel HV has the higher molecular weight, having a Brookfield viscosity of about 400 (1% water solution) to about 3500 (20%) water solution) centipoise wherein Kelco Gel LV has a viscosity of about 50 (1% solution) to about 250 (2% solution). Of these products, the Kelco Gel HV is highly preferred.

Preferably, the hydrocolloid is further clarified and sterilized before use by passage through a sterile filter having a pore size of 0.45 microns or smaller.

Preferably, the flow rates of gas and liquid are adjusted so that the size of the particles or droplets formed ranges from about 0.4 to about 2 mm in diameter. The flow rates depend to some extent on the viscosity of the liquid hydrocolloid, which in turn depends on the type and concentration of the hydrocolloid used. The provision of from about 0.4 to 2 millimeter particles, preferably about 0.6–1.5 millimeter particles, permits sufficient diffusion of nutrients and accessory growth factors into the particles to provide for cell growth. Substantially larger gel particles may decrease the growth and viability rates of the cells.

The concentration of hydrocolloid in the mixture should range from about 0.5 to about 1.4%, preferably about 0.6 to 1.2%, most preferably about 0.7–0.9%. This is considerably below percentages previously used, and is believed to result in higher porosity of the gel beads to nutrients and other factors. Attempts at making beads below 0.5 mm in diameter have met with difficulty, even with the fairly viscous Kelco Gel HV, and especially with Kelco Gel LV.

A key feature is to achieve cell-containing hydrogel beads with sufficient porosity and an appropriate size for diffusion of the nutrients to the cells in the inner reaches of the beads. While the Kelco Company products mentioned have been utilized in overcoming the problems of the prior art and growing mammalian cells in an encapsulated environment, many similar or alternative hydrogels exist in the art and are commercially available.

It having been shown that improved growth and viability rates can be obtained from such materials without use of the overcoating method of U.S. Pat. No. 4,391,909 (Lim) those skilled in the art can adjust the process to other similar materials. It is important that no semipermeable layer be formed on the outside of the hydrogel cell beads, either by cross linking of the hydrogel or by coating with a further polymer, for a number of reasons. Such coatings may interfere with the free diffusion into and out of the hydrogel beads. Moreover, the hydrogel beads of the present invention permit recycling and re-use of the cells contained therein, simply by dissolution of the hydrogel, which leaves the cells intact, and free from any non-cellular materials. This could not be done if the cells are enveloped in an insoluble polymer coating.

The spray head or nozzle utilized in connection with this invention need not be the modified hypodermic syringes used in previous products. Rather, standard off-the-shelf biphasic spray heads can be utilized to advantage in making the desired beads. Suitable spray heads include those sold by Spraying Systems, Inc., such as products sold under the designations ⅛ and JACN, ⅛ JACN ⅛ JBg. Other suitable nozzles are available in the art. Preferably, the nozzles used in this invention are beveled at the outside of this tip to form a conical tip, the sides are sloped at 15° or 30° to the longitudinal axis of the top, to direct the air flow at more of an angle to the droplets formed. Such an angle can be simply ground into the liquid tip orifice. Preferred inner diameters for the liquid spray tip include 0.006", 0.010" and 0.016", with the smaller sizes preferred, to produce smaller droplets.

One typical example of gel entrapment includes the steps of suspending cells at a concentration of about $10^6$ cells/ml in a 1.5% (w/v) solution of sodium alginate in normal saline. This suspension is placed in a suitably-sized vessel. Where the production run is to take considerable time, so that the cells will be out of contact with media for considerable time, nutrients and other materials can be added to the alginate suspension and/or to the multivalent gelling agent solution. A typical addition would include 50 mm of glucose, 1X of essential amino acids, 1X of nonessential amino acids, 1X of vitamins and/or any other needed growth factors. A tube from this vessel is connected to the liquid inlet of the spray head appartus. Another tube containing compressed air is connected to the air inlet of the spray head apparatus. The liquid is pumped through the spray head at the same time compressed air is blown through the spray head. The resultant sodium alginate cell suspension droplets are blown into the gelling solution of calcium chloride (1.0–1.3% (w/v)). The contact with calcium ions causes the immediate formation of a gel (calcium alginate) which entraps the cells contained within the gel droplet. Upon complete formation of all droplets, the droplets are removed from the calcium chloride solution, washed several times in normal saline solution and placed in the appropriate tissue culture medium. Entrapped cells have been shown to divide and metabolize for several weeks in these permanent calcium alginate gels. Cells are capable of attaining higher cell densities than if grown in normal tissue culture. The cell viabilities at these higher densities has also been shown to remain high (>50%).

In a preferred general process similar to that just described, seed cells for entrapment are cultured in conventional stir red-tank reactors as suspension cultures, typically in Iscove's Modified Dulbecco's Medium containing 5–10% (vol/vol) fetal bovine serum and 6 mM L-glutamine. Cells are harvested in the logarithmic phase of growth, at viabilities greater than or equal to 90%. All steps in the entrapment process are performed in laminar-flow cabinets providing HEPA-filtered air. Harvesting is done by pouring cell suspensions into sterile 800-ml glass centrifuge bottles and centrifuging for 10–15 minutes at 1500 rpm in an IEC CRU-5000 centrifuge to pellet the cells. All but 20–25 ml of the supernatant culture medium is removed by aspiration, and the cell pellets are gently resuspended in the remaining fluid. Sterile physiological saline and 1.0% (wt/vol) sodium alginate are then added to the pooled cells to effect a final alginate concentration of 0.8% (wt/vol), and a cell density of $2 \times 10^6$ cells per ml. The alginate-cell suspension is then extruded through a manifold droplet-forming apparatus (Spraying Systems 8490-SS) outfitted with four 1650SS liquid nozzles modified as outlined above, 64SS air caps, and needle valves to control liquid flow through the individual nozzles. The alginate-cell suspension is pumped through the manifold using a peristaltic pump (Cole-Parmer) and an airflow of 5 SCFH. Compressed air from a tank or in-house system is used, and sterilized by passage through a 0.22-micron hydrophobic filter before contacting the manifold. Droplet formation rate is controlled by pump speed and is typically on the order of 28–30 ml per minute per manifold. The alginate droplets thus formed fall into a receiving bath of sterile isotonic gelling solution composed of 1.3% calcium chloride dihydrate, 0.5% glucose, and 13 mM HEPES adjusted to pH 7.4. Exposure of the alginate droplets to the gelling solution causes the displacement of $Na+$ ions from the alginate by $Ca++$ ions and the formation of calcium alginate spheres, or beads, of 0.2–1.0 mm diameter. The alginate beads are transferred to a wash vessel and allowed to settle out of suspension. The supernatant gelling solution is aspirated from the beads and replaced with four times the settled bead volume of sterile physiological saline. This washing process is repeated three times; once more with sterile physiological saline, and twice with Iscove's Modified Dulbecco's Medium without Serum or L-glutamine. The last wash solution is removed and the beads resuspended in Iscove's Modified Dulbecco's Medium supplemented with 5–10% fetal bovine serum, 6 mM L-glutamine, and 50 ug/ml of gentamicin sulfate.

By-products from cell metabolism have been collected from gel-entrapped cell cultures produced by the above-described processes. For example, hybridoma cells (i.e. cells produced as a result of fusing spleen cells or antibody producing cells with a myeloma cell line either intra- or interspecies) may be entrapped in a calcium alginate gel-like material. These hybridoma cells may be obtained commercially, e.g. from the American Type Culture Collection, Rockville, Md., or may be prepared by any individual skilled in the art of tissue culture, immunology and hybridoma development. See ATCC Catalog, *Cell Lines, Viruses, Antisera,* 192 et seq (ATCC 1983); Kohler and Milstein, *Nature* 256: 495 (1975), the disclosure of which is incorporated herein by reference. Each individual hybridoma cell line may have its own unique set of growth requirements, i.e. type of tissue culture media and type and amount of nutrients required, as is recognized by individuals skilled in the art.

Under normal in vitro tissue culture conditions, most hybridoma cell lines grow to densities of $10^5$–$2 \times 10^6$ cells/ml of tissue culture media. These cells typically produce monoclonal antibodies in vitro at levels of 1–10 ug/ml/day of culture media depending on the cell line.

Growth of hybridoma cells to higher cell densities, as attained in the present invention, effectively increases the yield of monoclonal antibody/ml of culture media resulting in significant space and cost advantages. Entrapment of hybridoma cells in calcium alginate provides the means by which cell densities can be increased above $2 \times 10^6$ cell/ml and for production of monoclonal antibody at levels above the normal 1–10 ug/ml. One procedure achieving such production is described as follows:

Using aseptic procedures, cells from a particular hybridoma cell line are separated from their culture fluid by low speed centrifugation $(500 \times G)$ in sterile conical test tubes. The supernatant is removed and the cells are suspended to a concentration of $1 \times 10^5$–$2 \times 10^6$ cells/ml in a sodium alginate solution (e.g., Kelco Gel HV) at a concentration of 0.5–2.0%, preferably 0.6–1.5%, preferably in normal saline.

All work is carried out using aseptic techniques in a laminar flow hood. Air pressure is adjusted to 0.10 SCFH (standard cubic feet per hour) using the air flow meter 12 (e.g. Dwyer Flow Master #SS-2MHL-25). All equipment and tubing which the alginate cell suspension passes through has been sterilized. A 0.22 um in-line air filter (e.g. Millipore Millex-GS) sterilizes the air prior to its passage through the spray head assembly.

A sterile glass beaker containing an excess volume of sterile calcium chloride (0.65–1.5% w/v) is placed on a magnetic stirring plate below the spray head assembly such that the bottom of the spray head assembly is 5–10 inches about the surface of the calcium chloride solution. A sterile magnetic stir bar is placed in the calcium chloride. The magnetic stir plate is set at low speed.

The outflow tube of the peristaltic pump (e.g. Rainin "Rabbit") is connected to the liquid inlet of the spray head assembly, (e.g. Spraying Systems ⅛ JACN). The inlet tube of the peristaltic pump is inserted into the sodium alginate/cell suspension. The air tube is connected to the spray assembly and the air flow meter adjusted to 0–10 SCFH. The pump is turned on and adjusted so that the flow rate is 0–10 ml sodium alginate-cells/min. Droplets formed using this procedure fall into the solution of calcium chloride where sodium ions are replaced by the higher affinity calcium ions resulting in increased cross-linking of the alginate and formation of a stable calcium alginate gel containing entrapped hybridoma cells.

The procedure for washing alginate beads is as follows: After completion of the gelling reaction, the beads are allowed to settle out of suspension. The gelling solution is then removed by aspiration, and a volume of sterile physiological saline three times the volume of the settled beads added to the vessel. After the beads have resettled, the saline is aspirated and an additional three volumes of sterile saline added as above. This wash solution is aspirated, and two more washes are performed as above, except that sterile serum-free cell culture medium is used. Finally, the beads are resuspended in 5–10 volumes of culture medium containing all supplements (serum, L-glutamine, and antibiotics) and transferred to a culture vessel.

The gel-entrapped hybridoma cells are incubated at 37° C. and allowed to grow to their optimum cell density. The culture supernatant is removed and replaced with an equal volume of fresh supplemented culture growth medium as needed. Continuous feed systems may automatically replenish the media on a continuous basis. The entrapped hybridoma cells produce and secrete monoclonal antibody into the surrounding culture media. At optimum cell densities ($10^7$–$10^8$ cells/ml of calcium alginate), the hybridoma cells will produce antibody at the rate of 10–100 ug/ml/day or greater. The supernatant containing the monoclonal antibody may then be concentrated by conventional techniques to allow further purification of monoclonal antibody using techniques known by individuals skilled in the art.

The calcium alginate entrapped cells can be harvested and re-used by dilution of the calcium ions with chelating agents such as solutions of sodium citrate (10% w/v) ethylene diamine tetraacetic acid, (EDTA), sodium salt of ethylene glycol-bis (B-amino-ethyl ether N,N,N',N'-tetra acetic acid) (EGTA) which sequester or chelate the calcium ions causing reformation of the liquid sodium alginate. The hybridoma cells can then be harvested from the sodium alginate.

From the forgoing it will be apparent that the process for proliferating cells in an entrapped environment and harvesting cell products therefrom can be practiced for a wide variety of cells and cell products without departing from the scope and spirit of the invention. The following examples should accordingly be construed in all respects as illustrative and not in a limiting sense.

EXAMPLE I

Human red blood cells were added to a 1.2% sodium alginate solution to give a final concentration of $2.5 \times 10^5$ cells per ml in 1.0% sodium alginate. The solution was then conveyed by a Rainin Rabbit peristaltic pump to a sprayer assembly. Compressed air was supplied at 20 PSI through air tubing to a Dwyer airflow regulator and thereafter through 0.22 um filter (Millipore Millex-GS) and then to the sprayer assembly. Droplets were formed at the sprayer assembly which contained human red blood cells. The droplets were deposited in a sterile beaker containing a 1.33% w/v calcium chloride solution from a height of 3 cm. The beaker was stirred with a magnetic mixer at low speed and the droplets were allowed to gel. The gelled droplets were allowed to remain in the gelling solution for up to 30 minutes. The gelling solution was thereafter washed and the gelled droplets were resuspended in medium containing various concentrations of pyruvate and/or adenine in HEPES buffer. Red blood cells have been preserved in this fashion without hemolysis for 60 days.

EXAMPLE II

A hybridoma cell line was obtained from the American Type Culture Collection (ATCC). The cell line, designated as ATCC No. CRL-9017 (H25 B10) produces antibodies to Hepatitis B surface antigen (Ig $G_1$ Isotype). It's culture medium was a Dulbecco's Modified Eagles medium, 4.55 g/l glucose; and Fetal Bovine serum, 10% or less.

The gelling solution was prepared to have of final makeup of 1.3% $CaCl_2.2H_2O$, 0.5% glucose in 3 mM HEPES pH 7.7. A first wash solution contained a 1:1 mixture of the gelling solution with 0.9% saline. The second wash solution contained a 1:1 mixture of the first wash solution with 0.9 saline. The sodium alginate-cell suspension was a mixture of 1.2% sodium alginate with one part of cell suspension to make a final concentration of $2.0 \times 10^6$ cells per ml of sodium alginate.

The hybridoma cells from ATCC No. CRL-9017 (H25 B10) were encapsulated as follows:

The sodium alginate-hybridoma suspension was conveyed through the silastic 1/16" I.D. tubing by the peristaltic pump which was set at 350 to give a rate of approximately 2.5 ml rain to the sprayer. Air pressure was supplied to the sprayer assembly at 10–20 PSI. It was independently conveyed to the sprayer assembly by the 1/16" I.D. Silastic tubing through the Dwyer Gauge at 3 SCFH. From the air flow gauge the air passed through the Millex air filter to the spray assembly. (NB. all fittings from the air filter to the spray assembly were autoclaved at 15 PSI for 15 minutes). A beaker containing the gelling solution was placed directly below the spray assembly with a distance of about 3–4 cm between the spray orifice and the surface of the solution. A magnetic stir bar was placed in the beaker and the gelling solution agitated at low speed. Droplets of the sodium alginate-hybridoma suspension formed at the oriface of the spray assembly and dropped into the gelling solution where they were allowed to remain for about 3 minutes after the spraying operation. The gelling solution was then aspirated and the gel beads were resuspended in the first wash solution and allowed to settle. After 5 minutes the solution was aspirated in the same fashion as before. The gel beads were resuspended in the second wash solution and again aspirated. Upon completion of the washing evolution, the gel beads were placed in the above-described medium at a concentration of 20% gel beads.

The gel-entrapped hybridoma cells were incubated at 37° C. and allowed to grow to optimum densities in approximtely 11 days. At 3 day intervals or when phenol red indicator changed to yellow, the vessel fluids were aspirated and fresh nutrient media added. Fetal Bovine serum supplement was reduced from 10% to 0% at the third change of medium. The sequestered cluster of hybridoma cells excreted monoclonal antibodies (IgG) into the medium. The medium containing these antibodies was removed for harvest. The fluids were concentrated with 50% ammonium sulfate and further purified through affinity columns. The gel-entrapped cells were placed in a sodium citrate solution which converted the calcium alginate gel to sodium alginate liquid, releasing the hybridoma cells which were gel entrapped in a repeating cycle or production.

EXAMPLE III

A second hybridoma cell line was obtained from the ATCC with ATCC No. CRL-1644 (SJK-287-38). This cell line produces antibodies reactive with DNA polymerase alpha. It's culture medium was Dulbecco's Modified Eagles medium (10 mM) 100 ml; glutamine 100×, 1 ml; non-essential amino acids, 100×, 1 ml; NCTC109, 10 ml; Fetal bovine serum, 12 ml; and 1 ml of the solution prepared as follows:

a) 1320 mg oxaloacetic acid
b) 80 mg crystalline insulin (20 units/ml; 25 units 1 mg)
c) stir (a) and (b) at 37° C.
d) add 550 mg sodium pyruvate (50 mM0
e) bring to 100 ml with distilled water and continue stirring until dissolved (Filter and Sterilize).

These hybridomas were entrapped and propagated in gel beads as described in Example II.

EXAMPLE IV

A murine hybridoma cell line, designated as KTI-2A, produces antibodies to monoclonal antibodies. KTI-2A cell stocks were maintained in 500 ml spinner flasks in complete media (Iscove's media supplemented with 10% FBS, 6 mM L-glutamine, pencillin (50 U/ml) and streptomycin (50 mcg/ml)) at 37° C. Viabilities were >90%. $2 \times 10^8$ cells were prepared for gel encapsulation as follows by centrifugation at 800 rpm for 5 minutes. The media was aspirated and the cell pellet was loosened by gently flicking the centrifuge tube. The cells were resuspended in 20 ml of 0.9% NaCl. Thereafter, 80 ml of 1.0% Na alginate (Kelco-HV) was added and the cells mixed to form an even suspension. The final sodium alginate concentration of the suspension was 0.8%

Figure 2:
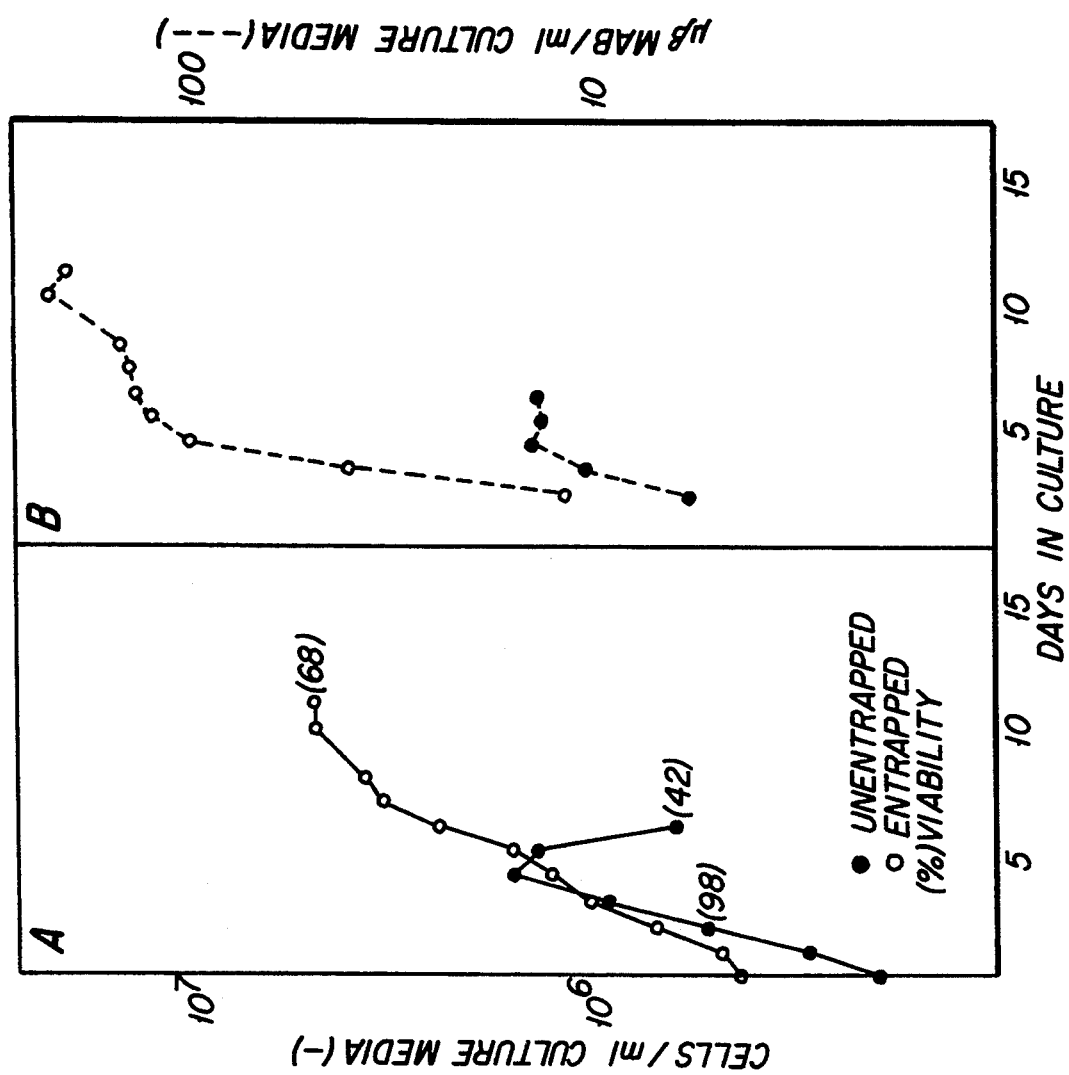
FIG. 2 depicts the growth, viability and antibody production of entrapped v. non-entrapped murine hybridoma cells designated KTI-2A.

The cell suspension was then delivered to a conventional two-phase spray head using a peristaltic pump. Sterile air was also delivered to the spray head at 3.5 SCFH. The alginate/cell droplets were propelled out of the spray head into a sterile beaker containing one liter of 1.2% $CaCl_2$ to form gel beads. The gel beads were washed twice with 0.9% NaCl and once with complete medium. Thereafter the gel beads were transferred to a 500 ml spinner flask and brought to a 500 ml final volume with complete medium and cultured at 37° C. Over a period of about two weeks, the cultures were fed as needed by replacing 50% of the spent-medium with fresh complete medium. The growth and viability of the gel entrapped hybridomas and antibody production are illustrated in FIG. 2 as compared with unentrapped cells established in complete media at $2 \times 10^6$ cells/ml. Entrapped cells were counted by dissolving a 0.5 ml aliquot of settled beads in 4.0 ml EDTA buffer (1% EDTA/0.5% NaCl, pH 7.1). Cells were counted in a hemacytometer. Viabilities were determined by dye exclusion. Antibody concentration secreted into the medium was measured by ELISA.

EXAMPLE V

Figure 3:
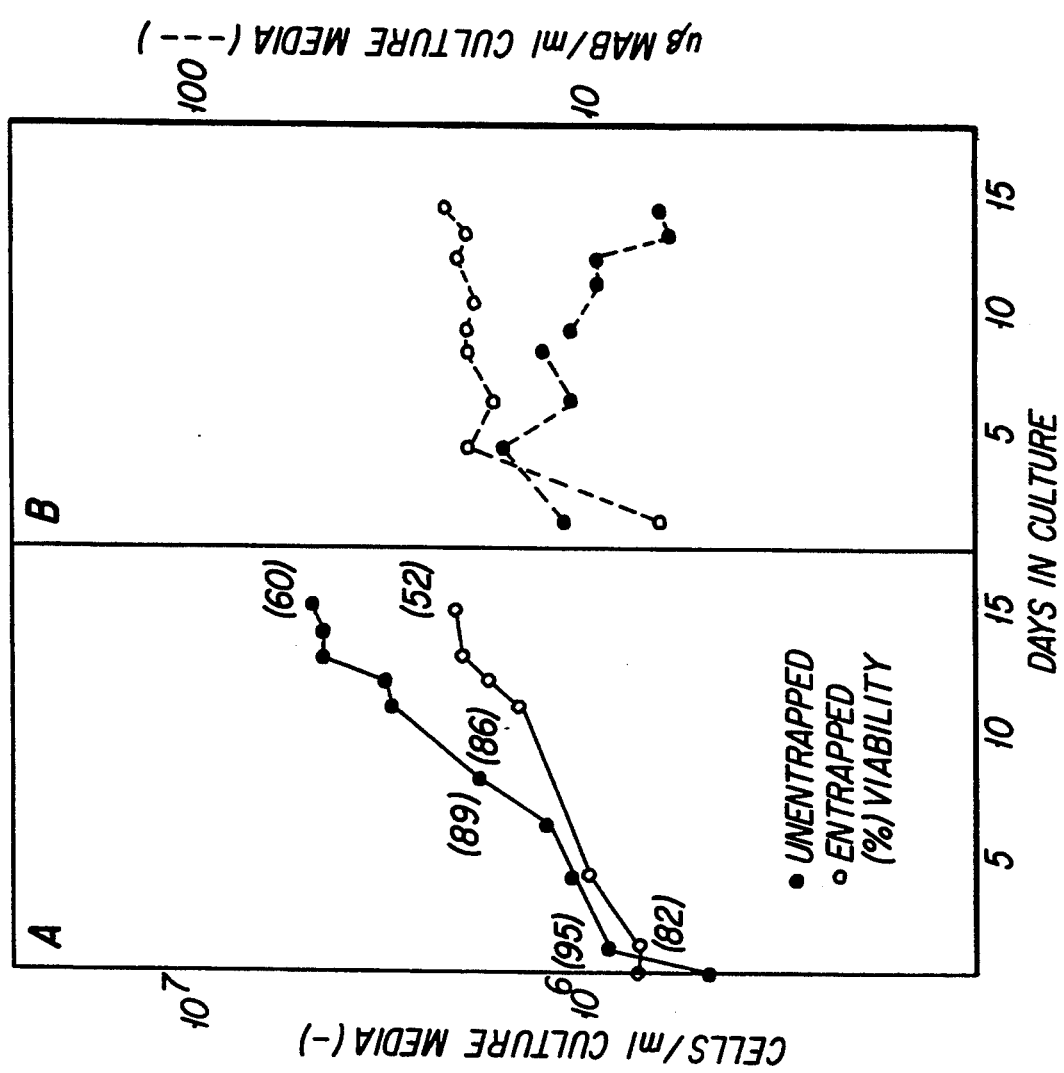
FIG. 3 depicts the growth, viability and antibody production of entrapped v. non-entrapped human B-cells designated KTI-7A.

Spontaneously transformed human B-cells, which secrete monoclonal IgM against human tumor cell antigen, designated KTI-7A, maintained in 850 $cm^2$ roller bottles at 37° C. in a standard roller apparatus were entrapped in accordance with the procedure set forth in Example IV. The growth, viability and antibody secretion of entrapped v. non-entrapped B-cells over a two-week period is illustrated in FIG. 3.

What is claimed is:

1. An apparatus for entrapping a biological material comprising:
    a) a biphasic spray head;
    b) means for admixing the biological material with a hydrophilic gel-forming material;
    c) means for delivering the admixture to the spray head;
    d) means for delivering a controlled source of air to the spray head; and
    e) means for receiving droplets formed by the spray head.

2. The apparatus of claim 1, wherein said spray head is provided with at least one nozzle having an inner diameter between about 0.006" and 0.016".

3. The apparatus of claim 2, wherein said nozzle is surrounded by an annular air passageway which delivers the controlled source of air to the spray head.

4. The apparatus of claim 2, wherein the nozzle is beveled at the outside to form a conical tip.

5. The apparatus of claim 4, wherein the nozzle is beveled at an angle between about 15° and 30° to the longitudinal axis of the nozzle.

6. An apparatus for entrapping a biological material comprising:
    (a) a biphasic spray head; wherein said biphasic sprayhead is provided with at least one nozzle having an inner diameter between about 0.006" and 0.016" and, wherein said nozzle is beveled at an angle between about 15° and 30° to the longitudinal axis of said nozzle at the outside to form a conical tip;
    (b) means for admixing the biological material with a hydrophilic gel-forming material;
    (c) means for delivering the admixture to the biphasic spray head;
    (d) an annular air passageway for delivering a controlled source of air to the biphasic spray head, said annular air passageway surrounding said nozzle; and
    (e) means for receiving droplets formed by the biphasic spray head.

* * * * *